US012098992B2

United States Patent
Sun et al.

(10) Patent No.: US 12,098,992 B2
(45) Date of Patent: Sep. 24, 2024

(54) EVALUATING SOURCE ROCK PERMEABILITY USING 3D MODEL

(71) Applicant: Saudi Arabian Oil Company, Dhahran (SA)

(72) Inventors: Qiushi Sun, Houston, TX (US); Shannon L. Eichmann, Katy, TX (US)

(73) Assignee: Saudi Arabian Oil Company, Dhahran (SA)

( * ) Notice: Subject to any disclaimer, the term of this patent is extended or adjusted under 35 U.S.C. 154(b) by 320 days.

(21) Appl. No.: 17/706,019

(22) Filed: Mar. 28, 2022

(65) Prior Publication Data
US 2022/0317015 A1    Oct. 6, 2022

Related U.S. Application Data

(60) Provisional application No. 63/168,813, filed on Mar. 31, 2021.

(51) Int. Cl.
| | |
|---|---|
| *G01N 15/08* | (2006.01) |
| *G01N 33/24* | (2006.01) |
| *G06T 15/08* | (2011.01) |

(52) U.S. Cl.
CPC ........... *G01N 15/088* (2013.01); *G01N 33/24* (2013.01); *G06T 15/08* (2013.01)

(58) Field of Classification Search
CPC ................ G01N 15/088; G01N 33/24; G01N 2015/0846; G06T 15/08; G06T 17/00
See application file for complete search history.

(56) References Cited

U.S. PATENT DOCUMENTS

| | | | | |
|---|---|---|---|---|
| 4,783,751 A * | 11/1988 | Ehrlich | ................ | G06V 20/695 |
| | | | | 345/581 |
| 5,671,136 A * | 9/1997 | Willhoit, Jr. | ............. | G01V 1/30 |
| | | | | 702/18 |
| 8,533,175 B2 * | 9/2013 | Roswell | ................ | G06F 16/958 |
| | | | | 707/741 |
| 8,818,778 B2 | 8/2014 | Salazar-Tio et al. | | |
| 9,182,511 B2 * | 11/2015 | Neave | .................... | G01V 1/345 |
| 9,507,047 B1 | 11/2016 | Dvorkin et al. | | |
| 11,093,544 B2 * | 8/2021 | Roswell | ................ | G06F 3/0481 |
| 2005/0171700 A1 * | 8/2005 | Dean | ...................... | G01V 1/301 |
| | | | | 702/16 |
| 2006/0235666 A1 * | 10/2006 | Assa | ...................... | G01V 11/00 |
| | | | | 703/10 |
| 2009/0187391 A1 | 7/2009 | Wendt et al. | | |

(Continued)

*Primary Examiner* — Tung S Lau
(74) *Attorney, Agent, or Firm* — Fish & Richardson P.C.

(57) ABSTRACT

A method for evaluating a rock permeability is disclosed. The method includes generating a binary 2D field of view image; selecting a plurality of regions from the generated image; locating a plurality of pores from the plurality of image seeds; collecting pore data for each pore of the plurality of pores; characterizing the pore data for each pore of the plurality of pores; storing pore data for each pore from the plurality of pores; choosing an image seed of the plurality of image seeds as an initial slice of the 3D image model of the source rock; modulating the pore data for each pore of the plurality of pores relative to the plurality of pores from each image seed of the plurality of image seeds; generating and combining the plurality of new images into a 3D volume to generate the 3D image model of the source rock.

20 Claims, 8 Drawing Sheets

(56) References Cited

U.S. PATENT DOCUMENTS

| | | | | |
|---|---|---|---|---|
| 2010/0128932 A1* | 5/2010 | Dvorkin | ............... | G01N 23/046 |
| | | | | 382/109 |
| 2014/0379119 A1* | 12/2014 | Sciacchitano | ...... | G05B 19/4099 |
| | | | | 700/182 |
| 2016/0125628 A1* | 5/2016 | Barnes | .................... | G06T 17/05 |
| | | | | 345/440 |
| 2020/0079143 A1* | 3/2020 | Bell | ......................... | B44F 9/04 |

* cited by examiner

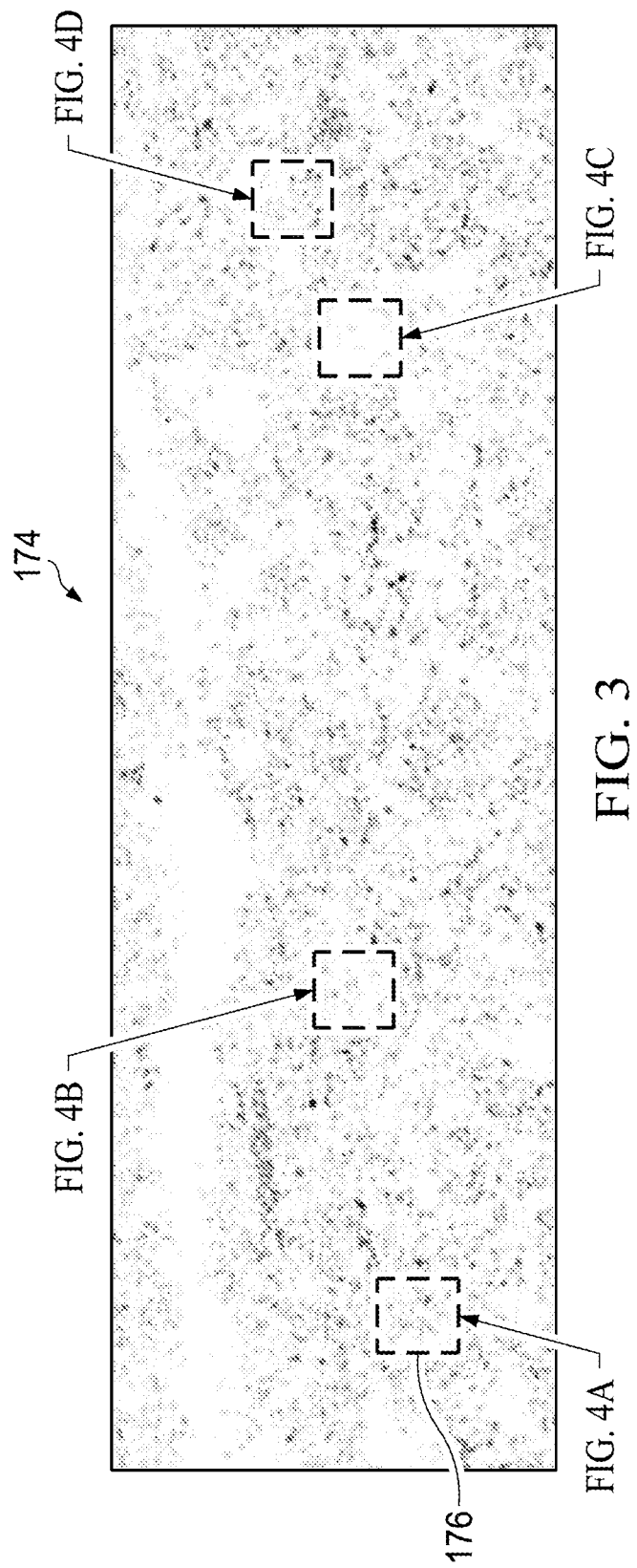

FIG. 5
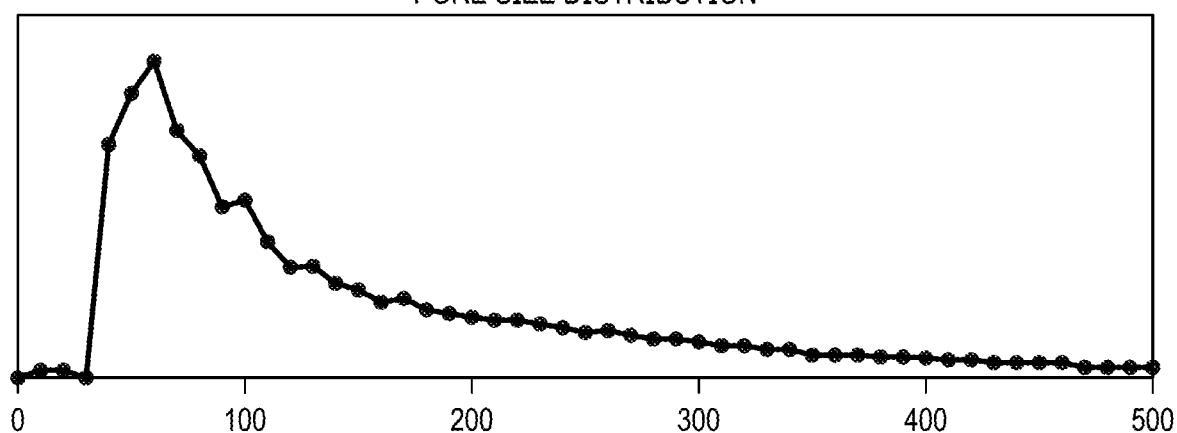
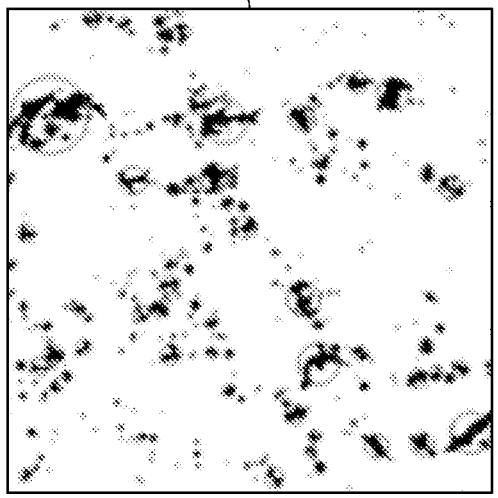
FIG. 6A
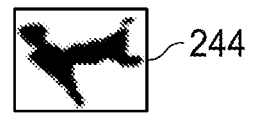
FIG. 6B
FIG. 6C
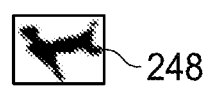
FIG. 6D

EVALUATING SOURCE ROCK PERMEABILITY USING 3D MODEL

CROSS REFERENCE TO RELATED APPLICATIONS

This application claims the benefit of U.S. Provisional Application Ser. No. 63/168,813, filed on Mar. 31, 2021, the entire content of which is incorporated herein by reference in its entirety.

TECHNICAL FIELD

The present disclosure generally relates to systems and methods for evaluating a source rock permeability in subsurface formation, more particularly evaluating a source rock permeability by generating a 3D image model.

BACKGROUND

Subsurface reservoirs are chemically heterogeneous where the rock matrix contains minerals and organic components that may contain pores. Pores developed in the organic matter are a result of cracking of organic matter after burial as the rock is compacted and exposed to elevated subsurface temperatures. Inorganic pores can result from mineral precipitation, grain compaction, or clay layering. In subsurface reservoirs that include shales, tight sands, and mudrocks, the pores can be on a nanoscale and the texture of the rock is heterogeneous.

Two-dimensional (2D) scanning electron microscopy (SEM) and three-dimensional (3D) focused ion beam (FIB) SEM are some methods used to study rock structures with significant micro- and nanoscale heterogeneity. Two-dimensional SEM images at high resolution cover a small field-of-view (FOV) and 3D FIB-SEM imaging collects a series of 2D small FOV images from the same sample surface. However, the porosity and the connected porosity of the source rock in 3D can considerably vary.

SUMMARY

This specification describes systems and methods for evaluating a rock permeability by generating a 3D image model of a source rock in a subsurface formation. The method allows evaluation of source rocks with high heterogeneity, angular and varied pore shapes, limited porosity, and limited connected porosity from subsurface formation. The method generates a 3D image model of the source rock using realistic data on the same scale as the laboratory experiments. It is important to generate realistic 3D images to supplement laboratory data collection instead of using inadequate amounts of laboratory data from a smaller scale (i.e. the nanoscale) to draw conclusions about properties on a larger scale for upscaling. Using realistic data makes it possible to accurately evaluate the petrophysical properties of source rocks with nanoscale heterogeneity and interpret the data with reference to the changing rock structure.

These methods use an extensive pore database generated from a large FOV 2D image to reseed pores and at the same time using erosion and dilation methods to change the size of existing pores in a model. The methods allow pores to grow and shrink with a size-dependent termination process resulting in a structure that mimics the connectivity, pore shape, and structure of real pore systems in subsurface formations.

In some aspects, a method for evaluating a rock permeability by generating a 3D image model of a source rock in a subsurface formation is disclosed. The method includes generating a binary 2D field of view image; selecting a plurality of regions from the generated binary 2D field of view image, each region of the plurality of regions serves as an image seed; locating a plurality of pores from the plurality of image seeds; collecting pore data for each pore of the plurality of pores; characterizing the pore data for each pore of the plurality of pores; storing pore data for each pore from the plurality of pores; choosing an image seed of the plurality of image seeds as an initial slice of the 3D image model of the source rock; modulating the pore data for each pore of the plurality of pores relative to the plurality of pores from each image seed of the plurality of image seeds; generating a plurality of new images from the plurality of image seeds by reseeding; and combining the plurality of new images into a 3D volume to generate the 3D image model of the source rock.

In some aspects, a computer program product for evaluating a rock permeability by generating a 3D image model of a source rock in a subsurface formation is disclosed. The computer program product includes generating a binary 2D field of view image; selecting a plurality of regions from the generated binary 2D field of view image, each region of the plurality of regions serves as an image seed; locating a plurality of pores from the plurality of image seeds; collecting pore data for each pore of the plurality of pores; characterizing the pore data for each pore of the plurality of pores; storing pore data for each pore from the plurality of pores; choosing an image seed of the plurality of image seeds as an initial slice of the 3D image model of the source rock; modulating the pore data for each pore of the plurality of pores relative to the plurality of pores from each image seed of the plurality of image seeds; generating a plurality of new images from the plurality of image seeds by reseeding; and combining the plurality of new images into a 3D volume to generate the 3D image model of the source rock.

Embodiments of the method and the computer program product for evaluating a rock permeability by generating a 3D image model of a source rock in a subsurface formation can include one or more of the following features.

In some embodiments, generating a binary 2D field of view image includes identifying a plurality of pores as a first value and identifying the rest of the binary 2D field of view image as a second value.

In some embodiments, selecting a plurality of regions from the generated binary 2D field of view image includes selecting regions with a pore size distribution similar to the pore size distribution from the generated binary 2D field of view image.

In some embodiments, collecting pore data for each pore of the plurality of pores includes collecting a location, a size, shape, and a perimeter for each pore.

In some embodiments, the method includes size-dependent pore terminating process. In some cases, the method includes retaining the data associated with the terminated pores that shrink below a specific size.

In some embodiments, the method includes selecting a plurality of random regions from the generated binary 2D field of view image.

In some embodiments, the method includes characterizing the pore data for each pore of the plurality of pores into small, medium, or large pores. In some cases, the method includes reseeding pores when the pore count drops below a threshold, and adds new small, medium, and large pores according to a distribution.

In some embodiments, the method includes simulating permeability of the source rock.

In some embodiments, the method includes simulating electrical and thermal conductivity of the source rock.

In some embodiments, the method includes correlating the pore data to mechanical and mineralogical data of the source rock.

The methods described in this specification can accurately evaluate rock permeability by providing a 3D representation of the source rock pore structure. The methods do not require prior knowledge of parameters such as electrical, elastic, capillary pressure, and permeability but rather characterize the pores in an existing slice and builds new slices based on the pore shapes seen in the previous slice. The methods also account for presence of new pore structures in subsequent images that are not present in the initial slice. This allows isolated pores to be included as well as a termination protocol for existing pores. The methods use real 2D images to generate 3D images by shifts, erosion, and dilation that produces images with realistic pore shapes at a reduced time.

The details of one or more embodiments of these methods are set forth in the accompanying drawings and the description below. Other features, objects, and advantages of these methods will be apparent from the description and drawings and from the claims.

DESCRIPTION OF DRAWINGS

FIG. 3 is an example of binary 2D FOV image of a source rock sample with pores generated using the equipment from FIG. 1.

FIG. 5 is an example of pore size distribution curve from a binary 2D FOV image such as shown in FIG. 3.

FIGS. 6A-6D show an example of modulating pore data according to a pore size distribution in a selected region.

DETAILED DESCRIPTION

This specification describes systems and methods for evaluating a rock permeability by generating a 3D image model of a source rock in a subsurface formation. The method allows evaluation of source rocks with high heterogeneity, angular and varied pore shapes, limited porosity, and limited connected porosity from subsurface formation. The method generates a 3D image model of the source rock using realistic data on the same scale as the laboratory experiments. It is important to generate realistic 3D images to supplement laboratory data collection instead of using inadequate amounts of laboratory data from a smaller scale (i.e. the nanoscale) to draw conclusions about properties on a larger scale for upscaling. Using realistic data makes it possible to accurately evaluate the petrophysical properties of source rocks with nanoscale heterogeneity and interpret the data with reference to the changing rock structure.

The methods allow connectivity between pores and termination of pores in a probabilistic way that mimics the real pore systems in subsurface formations. These methods use an extensive pore database generated from a large FOV 2D image to reseed pores and at the same time using erosion and dilation methods to change the size of existing pores in a model.

Figure 1A:
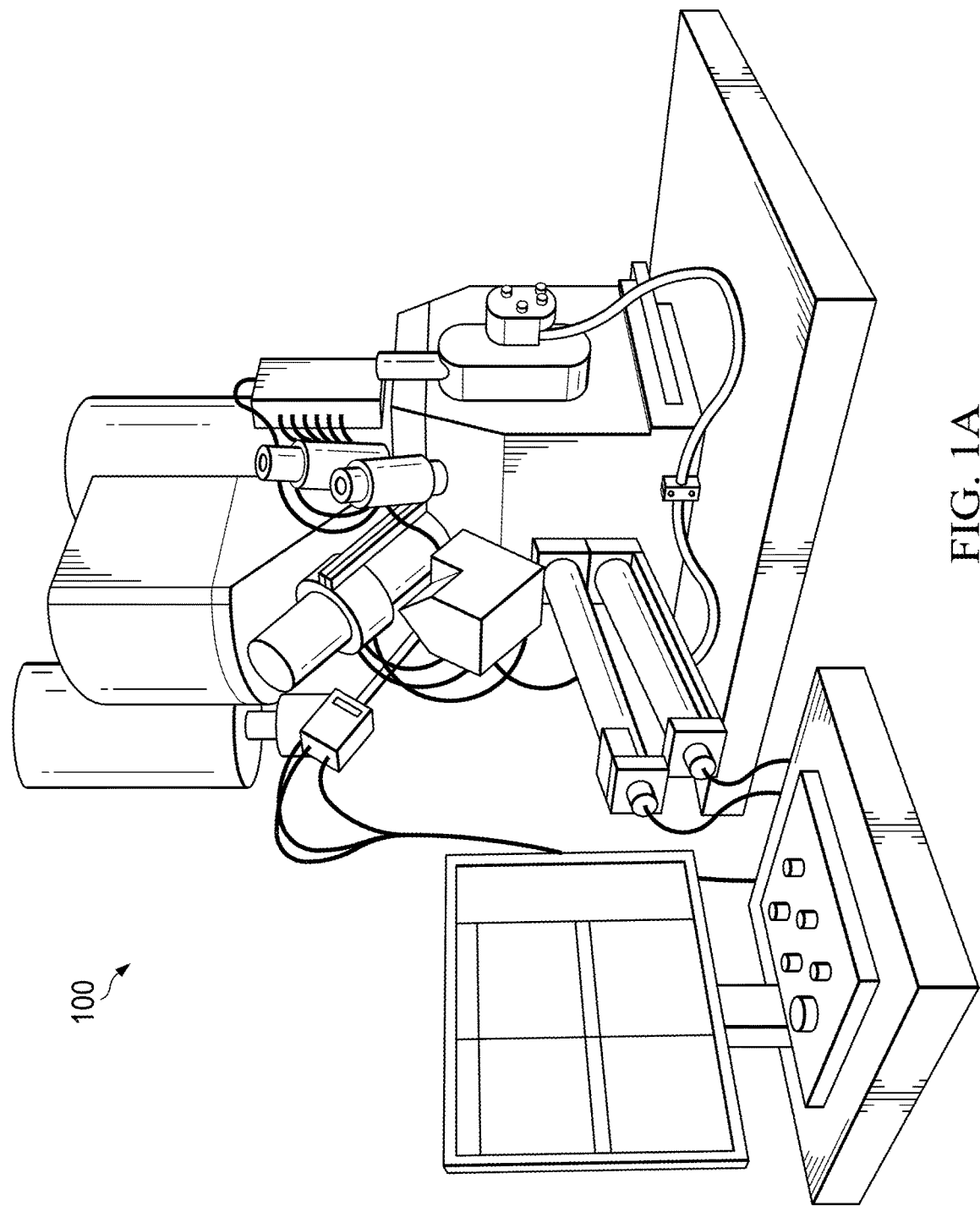
FIGS. 1A-1B are images of a SEM with FIB equipment, external and internal view, respectively.
Figure 1B:
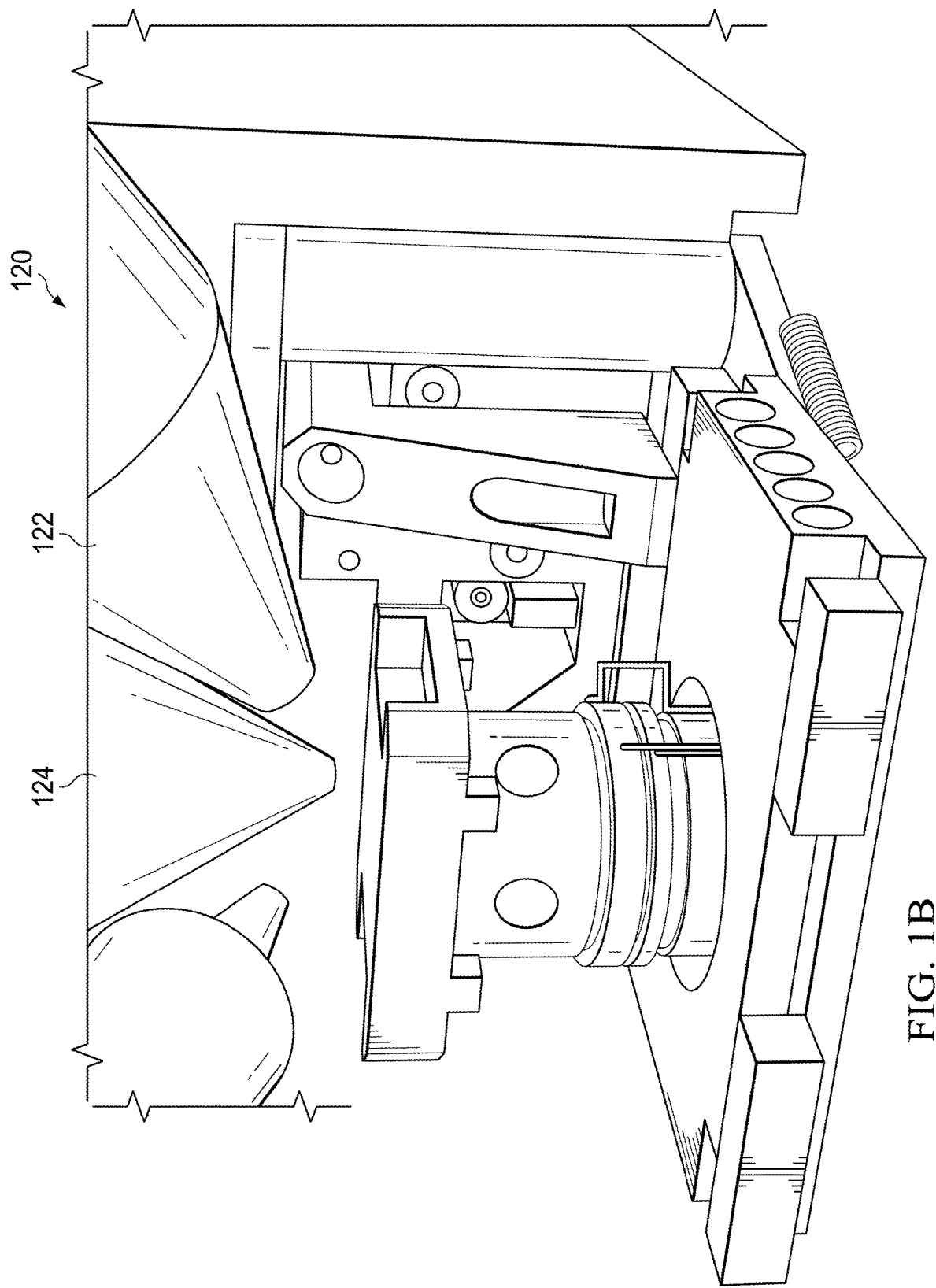

FIGS. 1A-1B are images of a SEM 100 with FIB equipment, external and internal 120 view, respectively. The SEM 100 can be used to evaluate a surface morphology and the structure of a source rock sample. The operating parameters of the SEM tool include the accelerating voltage at ~1 kV, the probe current at 40 pA, and the dwell time of 1500 ns. Each image is generated by the collection of the secondary electrons at the detector. The equipment 100 includes a focused ion beam (FIB) component 122 that can be used to cut/mill into the area of interest for a cross-sectional analysis of the source rock sample. In operation, the SEM 100 with the FIB 122 detects and identifies the area of interest on the sample surface and deposits platinum layer to define the start point of the milling location. Once the milling iterations are completed, the SEM captures 2D images. Parameters defined for milling include a tilt angle with a voltage of Ga ion beam 124 operating at a specified current. High-resolution SEM imaging can image a source rock with heterogeneous properties and nanoscale and microscale pores which are responsible for hydrocarbon storage and flow at this scale.

Two-dimensional SEM images at high resolution produce a small FOV. To increase the FOV, a series of 2D images can be collected and stitched together while maintaining high resolution. Similar to 2D SEM, 3D SEM with FIB imaging collects a series of 2D small FOV images. Rather than covering a large 2D area to increase lateral FOV the sample surface is milled between each image to expose a new part of the surface in the third dimension. After imaging, this series of images is aligned to generate a 3D rock volume which is then labeled to segment the various components of the rock (i.e., pores, organics, and matrix components). Sample preparation and imaging for large field of view (LgFOV) at high resolution 2D imaging with segmentation to analysis can take several days per image collected. If more analysis is added, for example, to analyze pore connectivity and flow through Digital Rock Physics (DRP) simulations, the additional sample preparation, imaging, alignment and segmentation can take a week or more. This does not include the time needed for subsequent flow analyses. In total, the time per sample for 2D imaging and subsequent 3D imaging can take several weeks not including full data analysis.

As a result, for each sample, a single large FOV image is collected by stitching a large number of adjacent secondary electron images and only one 3D FIB-SEM is collected. For example, the size of the each secondary electron image tile is approximately 4096 pixels×4096 pixel at 15 nm/pixel. More than 75 tiles are collected allowing for adjacent image overlap during alignment to generate an image around 800 um W×300 um H. In addition, the data size of the 3D FIB-SEM volumes at high resolution limits the FOV of these images to approximately tens of microns in the X, Y, and Z directions. For example, each 2D image is approximately 2000×2000 pixels at 10 nm/pixel and ~2000 image slices collected in the Z direction; this generates one 20 um×20 um×20 um 3D FIB-SEM image. However, after slice alignment and cropping to generate smooth cube edges the size of the cube is somewhat smaller than this starting volume size.

Because of the sizes of the 2D large FOV images, sufficient statistics to directly measure the compositional variations, porosity, and pore size distribution in source rock samples can be obtained. However, in 3D the porosity of the source rock can significantly vary. Generating a realistic 3D image model at a reduced computational time enables accurate evaluation of the heterogeneous properties of the source rock.

Figure 2:
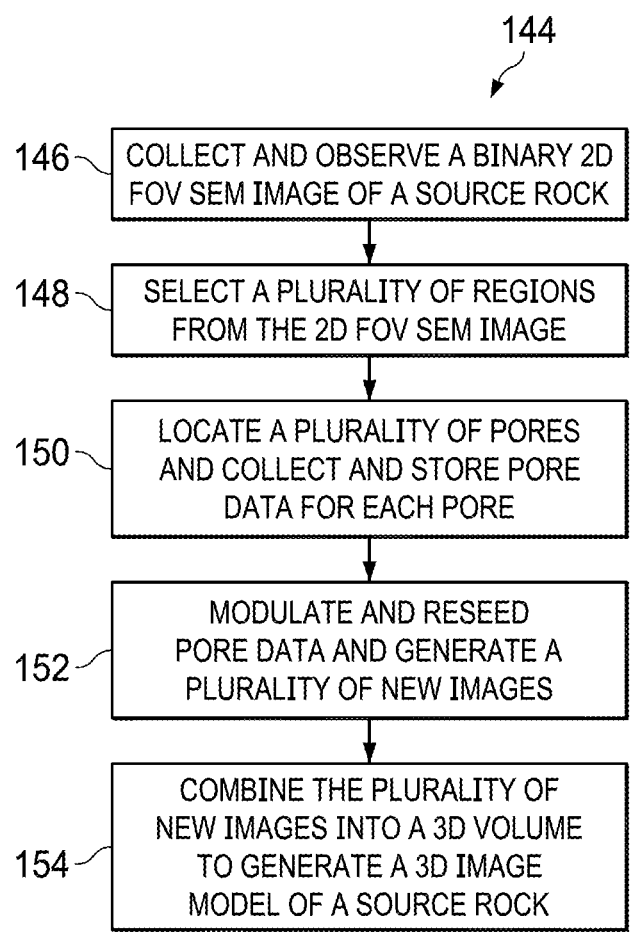
FIG. 2 is a flowchart representing a method for evaluating a source rock permeability in subsurface formation using a 3D image model.
Figure 4A:
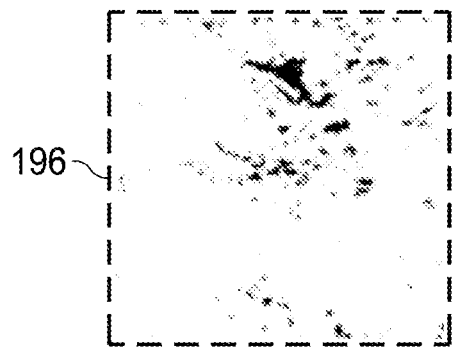
FIGS. 4A-4D illustrate selected regions from the binary 2D FOV image in FIG. 3 including various pore size distribution.
Figure 4B:
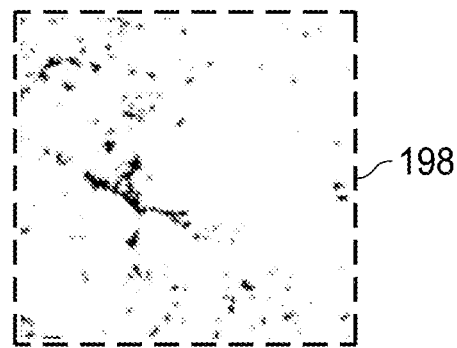
Figure 4C:
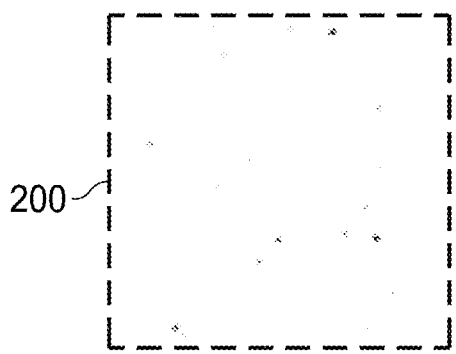
Figure 4D:
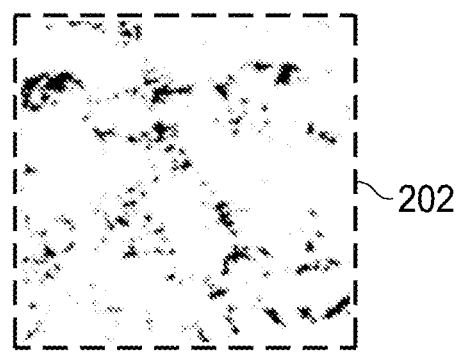

FIG. 2 is a flowchart representing a method 144 for evaluating a source rock permeability in subsurface formation using a 3D image model. The following discussion of the method describes the steps of the images collected with SEM/FIB equipment 100.

The method is based on an approach for evaluating a rock permeability by generating a 3D image model of a source rock in a subsurface formation. The method uses 2D FOV images to build a 3D image model of the source rock for evaluation. The image analysis are used to measure pore features and pore size distribution and the 3D image model is used in flow simulations to estimate permeability of the source rock.

In some implementations, the method includes collecting and observing binary 2D FOV images of a source rock (step 146). In the 2D FOV image, a plurality of pores are identified as the number one or white color and the rest of the image is identified as zero or black color. From the 2D FOV image, a plurality of regions are selected that can serve as image seeds (step 148). In some examples, the plurality of regions is randomly selected in a way that the pore size distribution is approximately similar to the pore size distribution of the 2D FOV image. The image seeds provide real pore structures that can be used in generation of the 3D image model. Each image seed is equivalent to the size of one slice of a 3D SEM-FIB image (e.g., 1000×1000 pixels). From the plurality of image seeds, one image seed is selected as the basis for the 3D image model generation and the rest of the images are used to provide real structures re-populating pores when needed in the 3D structure to better mimic small isolated pores and new pores that may appear deeper into the 3D image.

FIG. 3 is an example of binary 2D FOV image 174 of a source rock sample with pores generated using the equipment 100 from FIGS. 1A-1B. As illustrated, a plurality of regions 176 are selected from the 2D FOV image 174. FIGS. 4A-4D illustrate selected regions 196, 198, 200, and 202 from the 2D FOV image 174 in FIG. 3 including various pore size distributions in each region. FIG. 5 is an example of a pore size distribution curve 222 from the 2D FOV image 174 in FIG. 3.

In some implementations, the method includes locating a plurality of pores from each image seed of a plurality of image seeds, collecting, characterizing and storing pore data for each pore of the plurality of pores (step 150). The pore data includes the location and size of the bounding box for each pore, the indexed binary data for pore pixels, the pore area, the pore diameter (i.e. equivalent circular diameter), the pore orientation, the pore perimeter, and other similar structural identifiers. This creates a database of pore shapes and sizes from a wide selection of seeds. The pores are also sorted into size groupings: small (e.g., less than 25 pixels in area), medium (e.g., between 25 and 100 pixels in area), and large (e.g., greater than 100 pixels in area). From the plurality of seed images one seed is selected to serve as the initial or base slice for generating the 3D image model. The pore properties are collected again for the selected initial seed.

However, the pore data is modulated for each pore of the plurality of pores and a plurality of new images are generated by reseeding (step 152). Each pore in the previous slice is modulated according to a distribution. This distribution determines the magnitude and direction the centroid will shift, and a separate distribution will determine how the pore's borders will change. The pore can shrink or grow on any of its borders and change its shape. In some examples, the limits for the shift, growth, and shrinking is user defined. In other examples, they can be randomly assigned or based on other known or expected information on tortuosity or pore structural variations. A modified erosion and dilation process allows for changing pore size along the pore path while shifts impart tortuosity.

The modified erosion and dilation image morphology processes are detailed as follows. Because pores are 1 and non-pores are 0, each pixel is summed with its 8 nearest neighboring pixels. This generates a topographical matrix where erosions occur when pixels are under a user-specified threshold, and dilations occur when pixels are above a user-specified threshold. A random value from a user-defined range is added to each pixel to add texture to the edges so erosions and dilations are not uniform, which tends toward generating smooth linear features. This makes edges tend to be amorphous (i.e. more realistic) and prevents corners from dominating the modulated pore structures. For each side, the process is done a number of times chosen randomly from a user-defined range to prevent overly regular erosions and dilations.

When combined, these allow for pore coalescence as well as pores to cross lateral boundaries and imparting connectivity in the perpendicular directions. In some implementations, the method can include a pore termination step that is probabilistic dependent upon the area of the pore. The termination is used to avoid tailing pore features which are not often found in real rock structures from these rock types. While it is possible for large pores to abruptly terminate, smaller pores are far more likely to terminate randomly as well as become eroded to the point of the pore diameter being zero. The pores that shift outside of the boundaries are still retained, and may return to the target image area at a later point. To compensate for the loss of pores, each slice is reseeded to approximately retain the same number of pores as the original slice, with pores being reseeded according to a distribution. For example, if the pore count were to fall below 80% of the number of pores in the original seed regardless of size, enough pores to repopulate the image up to 120% of the number of pores present in the original seed can be added. The distribution can be, for example, 60% small pores, 30% medium pores, and 10% large pores, where the pore sizes are taken from the small, medium, and large lists of pores from the stored data (step 150). This step also compensates for the loss of pores that have coalesced as well as those that have left the bounding box and not yet or may not reenter.

FIGS. 6A-6D show an example of modulating pore data according to a pore distribution in a selected region. As illustrated, the initial slice 242 is selected and the pore data is collected. The pore data is modulated and new images 244, 246, and 248 with various sizes, shapes, and shrinkage are populated and stored. The stored information can be located for reseeding of another image with new pores.

Figure 7:
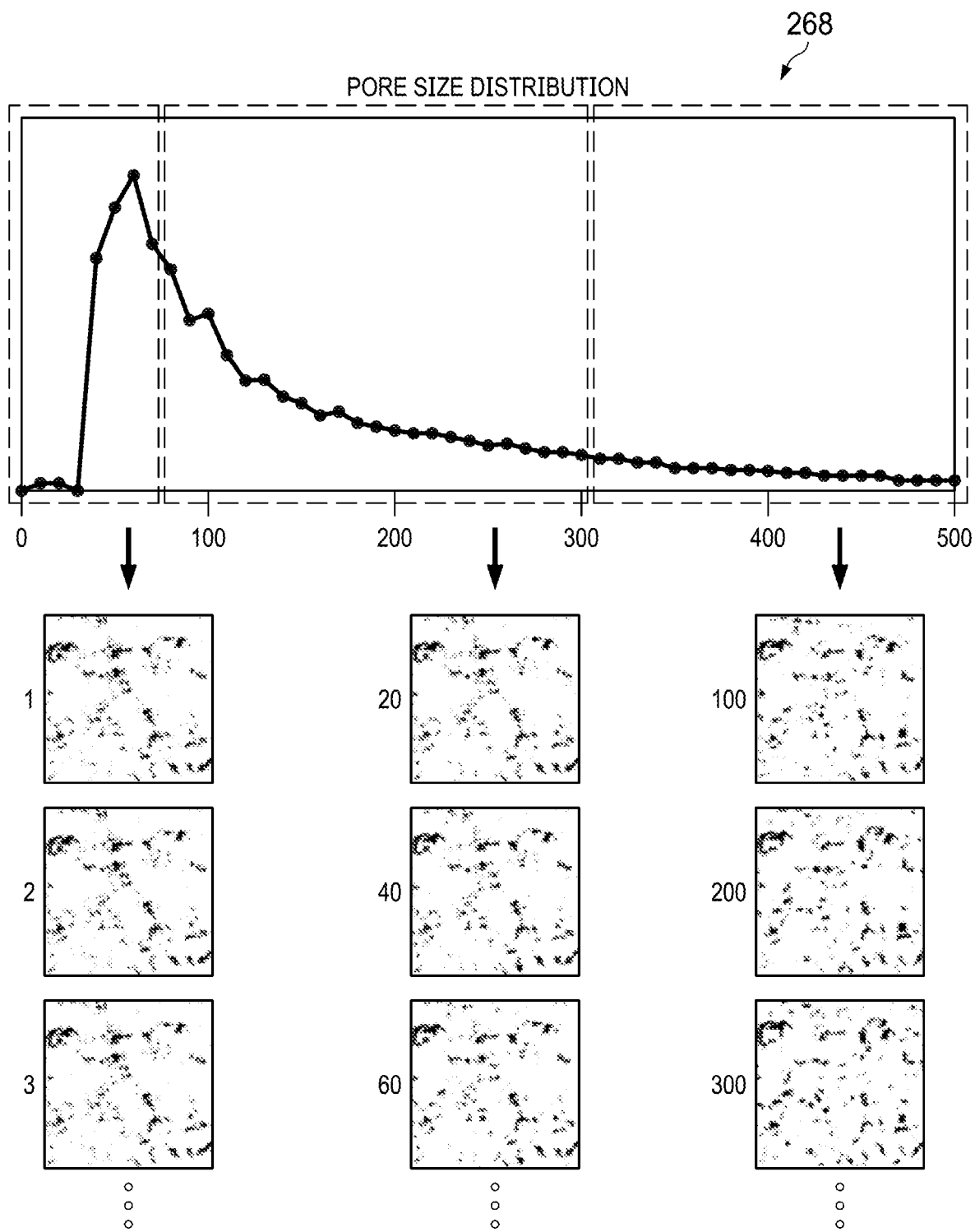
FIG. 7 shows an example of reseeding new images using various frequencies for pore size distribution.

FIG. 7 shows an example of reseeding new images 268 using various frequencies for pore distribution. As illustrated, method steps 146-152 are repeated many times over for each subsequent slice. Reseeding frequency can be defined to fit a need. In this example, a number of pores are seeded whenever the number of pores in the image (including pores that move outside the displayed image area) drops below 80% of the number of pores in the initial slice. The actual number of pores seeded is first randomized to repopulate a number of pores in the image to between 80% and 120% of the pores in the initial slice. The proportion of the new pores seeded follow a distribution (60% small, 30% medium, and 10% large). Because of the randomized nature of the reseeding and the dependency on the number of pores, it prevents the porosity in the image from immediately dropping off as well as keeping the reseeding intervals irregular, both of which are realistic These pores are seeded according to a probability distribution to prevent exactly regular reseeding intervals. Reseeding also serves the purpose to impart realistic abrupt pore shape changes as seen in real rock volumes. Since the reseeding on a new pore may overlay an existing pore structure, a single pore can have considerable morphology changes. For each slice following reseeding or termination, all pores are located, features detected, and the shift, erosion, and dilation is repeated to generate a new image. For each iteration the seed image, subsequent generated images, and pore feature data are written to a known location where the data is available for future use. This is repeated many times to generate many realizations starting from many seeds. Each series of images is combined or rendered to a 3D volume to generate the 3D image model of the source rock for evaluating a rock permeability (step 154). In some implementations, the method includes simulating permeability of the source rock. In some implementations, the method includes simulating electrical and thermal conductivity of the source rock. In some implementations, the method includes correlating the pore data to mechanical and mineralogical data of the source rock.

In summary, the described method allows generating many 3D cubic images in less time using selected seed images from the 2D FOV image. It takes significantly less time to acquire one 2D FOV image than a single 3D image. The average time required to generate a single 2D FOV image is on the order of 24 hours with sample preparation and imaging, compared to one the order or several days for sample preparation and acquisition time for a single cube from a FIB-SEM. In addition, the 2D FOV images contains significantly more pores (hundreds of thousands) than a single 3D cubic image (about a thousand pores or less) and are considered to be representative of the porosity of the larger scale. This large time difference required for the 3D image collection leads to only one or very few 3D images to be collected per each 2D FOV image and the heterogeneity of the sample cannot be captured fully in the typical 3D image volumes collected for source rocks. The method described allows many 3D images with specific features to be created from a single 2D FOV image while saving time and improving statistical sampling of the potential pore space heterogeneity that affects fluid flow. This removes the limitation of attaining the large number of unique rock volumes needed to estimate the permeability of the rock from 3D images. Rather than relying on the permeability from a single or very few 3D image volumes that are hand-picked to contain well developed pores in the 2D image. The permeability can be estimated by many more realizations including those where the 2D image may contain limited porosity thus improving statistical sampling. These types of realizations are required as training data for various machine learning efforts in digital rock physics where collecting the required number of real 3D volumes is not feasible.

Figure 8:
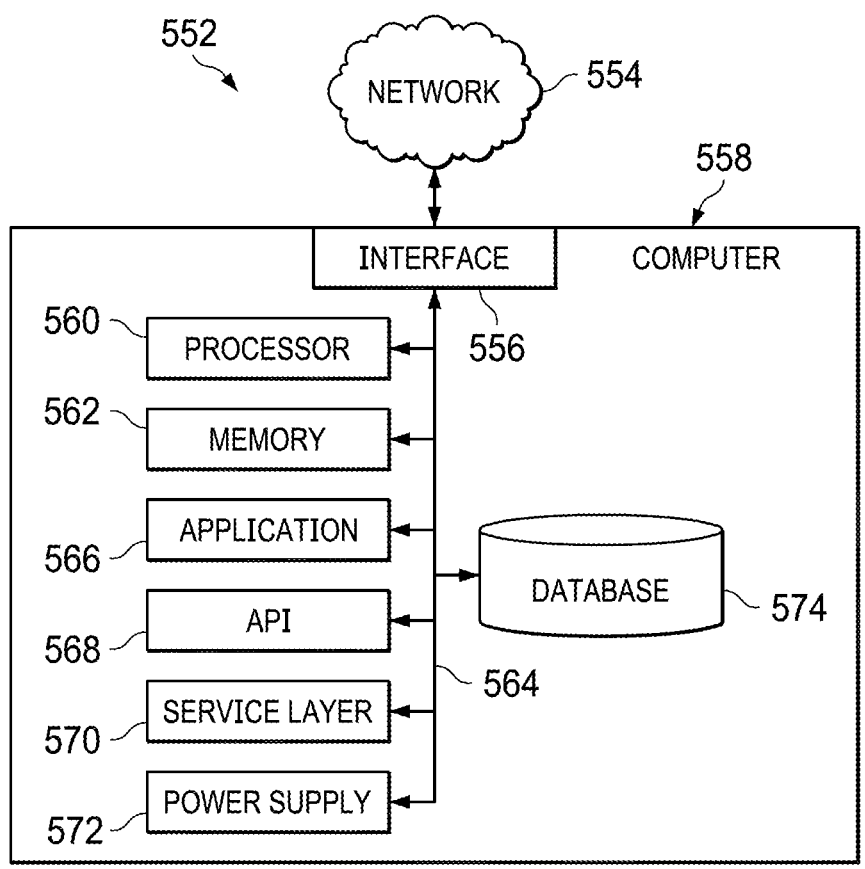
FIG. 8 is a block diagram of an example computer system.

FIG. 8 is a block diagram of an example computer system 552 used to provide computational functionalities associated with described algorithms, methods, functions, processes, flows, and procedures described in the present disclosure, according to some implementations of the present disclosure. The illustrated computer 558 is intended to encompass any computing device such as a server, a desktop computer, a laptop/notebook computer, a wireless data port, a smartphone, a personal data assistant (PDA), a tablet computing device, or one or more processors within these devices, including physical instances, virtual instances, or both. The computer 558 can include input devices such as keypads, keyboards, and touch screens that can accept user information. Also, the computer 558 can include output devices that can convey information associated with the operation of the computer 558 The information can include digital data, visual data, audio information, or a combination of information. The information can be presented in a graphical user interface (UI) (or GUI).

The computer 558 can serve in a role as a client, a network component, a server, a database, a persistency, or components of a computer system for performing the subject matter described in the present disclosure. The illustrated computer 558 is communicably coupled with a network 554. In some implementations, one or more components of the computer 558 can be configured to operate within different environments, including cloud-computing-based environments, local environments, global environments, and combinations of environments.

At a high level, the computer 558 is an electronic computing device operable to receive, transmit, process, store, and manage data and information associated with the described subject matter. According to some implementations, the computer 558 can also include, or be communicably coupled with, an application server, an email server, a web server, a caching server, a streaming data server, or a combination of servers.

The computer 558 can receive requests over network 554 from a client application (for example, executing on another computer 558). The computer 558 can respond to the received requests by processing the received requests using software applications. Requests can also be sent to the computer 558 from internal users (for example, from a command console), external (or third) parties, automated applications, entities, individuals, systems, and computers. Each of the components of the computer 558 can communicate using a system bus 564. In some implementations, any or all of the components of the computer 558, including hardware or software components, can interface with each other or the interface 556 (or a combination of both), over the system bus 564. Interfaces can use an application programming interface (API) 568, a service layer 570, or a combination of the API 568 and service layer 570. The API 568 can include specifications for routines, data structures, and object classes. The API 568 can be either computer-language independent or dependent. The API 568 can refer to a complete interface, a single function, or a set of APIs.

The service layer 570 can provide software services to the computer 558 and other components (whether illustrated or not) that are communicably coupled to the computer 558. The functionality of the computer 558 can be accessible for all service consumers using this service layer. Software services, such as those provided by the service layer 570, can provide reusable, defined functionalities through a defined interface. For example, the interface can be software written in JAVA, C++, or a language providing data in extensible markup language (XML) format. While illustrated as an integrated component of the computer 558, in alternative implementations, the API 568 or the service layer 570 can be stand-alone components in relation to other components of the computer 558 and other components communicably coupled to the computer 558. Moreover, any or all parts of the API 568 or the service layer 570 can be implemented as child or sub-modules of another software module, enterprise application, or hardware module without departing from the scope of the present disclosure.

The computer 558 includes an interface 556. Although illustrated as a single interface 556 in FIG. 8, two or more interfaces 556 can be used according to particular needs, desires, or particular implementations of the computer 558 and the described functionality. The interface 556 can be used by the computer 558 for communicating with other systems that are connected to the network 554 (whether illustrated or not) in a distributed environment. Generally, the interface 556 can include, or be implemented using, logic encoded in software or hardware (or a combination of software and hardware) operable to communicate with the network 554. More specifically, the interface 556 can include software supporting one or more communication protocols associated with communications. As such, the network 554 or the interface's hardware can be operable to communicate physical signals within and outside of the illustrated computer 558.

The computer 558 includes a processor 560. Although illustrated as a single processor 560 in FIG. 8, two or more processors 560 can be used according to particular needs, desires, or particular implementations of the computer 558 and the described functionality. Generally, the processor 560 can execute instructions and can manipulate data to perform the operations of the computer 558, including operations using algorithms, methods, functions, processes, flows, and procedures as described in the present disclosure.

The computer 558 also includes a database 574 that can hold data for the computer 558 and other components connected to the network 554 (whether illustrated or not). For example, database 574 can be an in-memory, conventional, or a database storing data consistent with the present disclosure. In some implementations, database 574 can be a combination of two or more different database types (for example, hybrid in-memory and conventional databases) according to particular needs, desires, or particular implementations of the computer 558 and the described functionality. Although illustrated as a single database 574 in FIG. 8, two or more databases (of the same, different, or combination of types) can be used according to particular needs, desires, or particular implementations of the computer 558 and the described functionality. While database 574 is illustrated as an internal component of the computer 558, in alternative implementations, database 574 can be external to the computer 558.

The computer 558 also includes a memory 562 that can hold data for the computer 558 or a combination of components connected to the network 554 (whether illustrated or not). Memory 562 can store any data consistent with the present disclosure. In some implementations, memory 562 can be a combination of two or more different types of memory (for example, a combination of semiconductor and magnetic storage) according to particular needs, desires, or particular implementations of the computer 558 and the described functionality. Although illustrated as a single memory 562 in FIG. 8, two or more memories 562 (of the same, different, or combination of types) can be used according to particular needs, desires, or particular implementations of the computer 558 and the described functionality. While memory 562 is illustrated as an internal component of the computer 558, in alternative implementations, memory 562 can be external to the computer 558.

The application 566 can be an algorithmic software engine providing functionality according to particular needs, desires, or particular implementations of the computer 558 and the described functionality. For example, application 566 can serve as one or more components, modules, or applications. Further, although illustrated as a single application 566, the application 566 can be implemented as multiple applications 566 on the computer 558. In addition, although illustrated as internal to the computer 558, in alternative implementations, the application 566 can be external to the computer 558.

The computer 558 can also include a power supply 572. The power supply 572 can include a rechargeable or non-rechargeable battery that can be configured to be either user- or non-user-replaceable. In some implementations, the power supply 572 can include power-conversion and management circuits, including recharging, standby, and power management functionalities. In some implementations, the power-supply 572 can include a power plug to allow the computer 558 to be plugged into a wall socket or a power source to, for example, power the computer 558 or recharge a rechargeable battery.

There can be any number of computers 558 associated with, or external to, a computer system containing computer 558, with each computer 558 communicating over network 554. Further, the terms "client," "user," and other appropriate terminology can be used interchangeably, as appropriate, without departing from the scope of the present disclosure. Moreover, the present disclosure contemplates that many users can use one computer 558 and one user can use multiple computers 558.

Implementations of the subject matter and the functional operations described in this specification can be implemented in digital electronic circuitry, intangibly embodied computer software or firmware, in computer hardware, including the structures disclosed in this specification and their structural equivalents, or in combinations of one or more of them. Software implementations of the described subject matter can be implemented as one or more computer programs. Each computer program can include one or more modules of computer program instructions encoded on a tangible, non-transitory, computer-readable computer-storage medium for execution by, or to control the operation of, data processing apparatus. Alternatively, or additionally, the program instructions can be encoded in/on an artificially-generated propagated signal. The example, the signal can be a machine-generated electrical, optical, or electromagnetic signal that is generated to encode information for transmission to suitable receiver apparatus for execution by a data processing apparatus. The computer-storage medium can be a machine-readable storage device, a machine-readable storage substrate, a random or serial access memory device, or a combination of computer-storage mediums.

The terms "data processing apparatus," "computer," and "electronic computer device" (or equivalent as understood by one of ordinary skill in the art) refer to data processing hardware. For example, a data processing apparatus can encompass all kinds of apparatus, devices, and machines for processing data, including by way of example, a programmable processor, a computer, or multiple processors or computers. The apparatus can also include special purpose logic circuitry including, for example, a central processing unit (CPU), a field programmable gate array (FPGA), or an application specific integrated circuit (ASIC). In some implementations, the data processing apparatus or special purpose logic circuitry (or a combination of the data processing apparatus or special purpose logic circuitry) can be hardware- or software-based (or a combination of both hardware- and software-based). The apparatus can optionally include code that creates an execution environment for computer programs, for example, code that constitutes processor firmware, a protocol stack, a database management system, an operating system, or a combination of execution environments. The present disclosure contemplates the use of data processing apparatuses with or without conventional operating systems, for example LINUX, UNIX, WINDOWS, MAC OS, ANDROID, or IOS.

A computer program, which can also be referred to or described as a program, software, a software application, a module, a software module, a script, or code, can be written in any form of programming language. Programming languages can include, for example, compiled languages, interpreted languages, declarative languages, or procedural languages. Programs can be deployed in any form, including as stand-alone programs, modules, components, subroutines, or units for use in a computing environment. A computer program can, but need not, correspond to a file in a file system. A program can be stored in a portion of a file that holds other programs or data, for example, one or more scripts stored in a markup language document, in a single file dedicated to the program in question, or in multiple coordinated files storing one or more modules, sub programs, or portions of code. A computer program can be deployed for execution on one computer or on multiple computers that are located, for example, at one site or distributed across multiple sites that are interconnected by a communication network. While portions of the programs illustrated in the various figures may be shown as individual modules that implement the various features and functionality through various objects, methods, or processes, the programs can instead include a number of sub-modules, third-party services, components, and libraries. Conversely, the features and functionality of various components can be combined into single components as appropriate. Thresholds used to make computational determinations can be statically, dynamically, or both statically and dynamically determined.

The methods, processes, or logic flows described in this specification can be performed by one or more programmable computers executing one or more computer programs to perform functions by operating on input data and generating output. The methods, processes, or logic flows can also be performed by, and apparatus can also be implemented as, special purpose logic circuitry, for example, a CPU, an FPGA, or an ASIC.

Computers suitable for the execution of a computer program can be based on one or more of general and special purpose microprocessors and other kinds of CPUs. The elements of a computer are a CPU for performing or executing instructions and one or more memory devices for storing instructions and data. Generally, a CPU can receive instructions and data from (and write data to) a memory. A computer can also include, or be operatively coupled to, one or more mass storage devices for storing data. In some implementations, a computer can receive data from, and transfer data to, the mass storage devices including, for example, magnetic, magneto optical disks, or optical disks. Moreover, a computer can be embedded in another device, for example, a mobile telephone, a personal digital assistant (PDA), a mobile audio or video player, a game console, a global positioning system (GPS) receiver, or a portable storage device such as a universal serial bus (USB) flash drive.

Computer readable media (transitory or non-transitory, as appropriate) suitable for storing computer program instructions and data can include all forms of permanent/non-permanent and volatile/non-volatile memory, media, and memory devices. Computer readable media can include, for example, semiconductor memory devices such as random access memory (RAM), read only memory (ROM), phase change memory (PRAM), static random access memory (SRAM), dynamic random access memory (DRAM), erasable programmable read-only memory (EPROM), electrically erasable programmable read-only memory (EEPROM), and flash memory devices. Computer readable media can also include, for example, magnetic devices such as tape, cartridges, cassettes, and internal/removable disks. Computer readable media can also include magneto optical disks and optical memory devices and technologies including, for example, digital video disc (DVD), CD ROM, DVD+/-R, DVD-RAM, DVD-ROM, HD-DVD, and BLU-RAY. The memory can store various objects or data, including caches, classes, frameworks, applications, modules, backup data, jobs, web pages, web page templates, data structures, database tables, repositories, and dynamic information. Types of objects and data stored in memory can include parameters, variables, algorithms, instructions, rules, constraints, and references. Additionally, the memory can include logs, policies, security or access data, and reporting files. The processor and the memory can be supplemented by, or incorporated in, special purpose logic circuitry.

Implementations of the subject matter described in the present disclosure can be implemented on a computer having a display device for providing interaction with a user, including displaying information to (and receiving input from) the user. Types of display devices can include, for example, a cathode ray tube (CRT), a liquid crystal display (LCD), a light-emitting diode (LED), and a plasma monitor. Display devices can include a keyboard and pointing devices including, for example, a mouse, a trackball, or a trackpad. User input can also be provided to the computer through the use of a touchscreen, such as a tablet computer surface with pressure sensitivity or a multi-touch screen using capacitive or electric sensing. Other kinds of devices can be used to provide for interaction with a user, including to receive user feedback, for example, sensory feedback including visual feedback, auditory feedback, or tactile feedback. Input from the user can be received in the form of acoustic, speech, or tactile input. In addition, a computer can interact with a user by sending documents to, and receiving documents from, a device that is used by the user. For example, the computer can send web pages to a web browser on a user's client device in response to requests received from the web browser.

The term "graphical user interface," or "GUI," can be used in the singular or the plural to describe one or more graphical user interfaces and each of the displays of a particular graphical user interface. Therefore, a GUI can represent any graphical user interface, including, but not limited to, a web browser, a touch screen, or a command line interface (CLI) that processes information and efficiently presents the information results to the user. In general, a GUI can include a plurality of user interface (UI) elements, some or all associated with a web browser, such as interactive fields, pull-down lists, and buttons. These and other UI elements can be related to or represent the functions of the web browser.

Implementations of the subject matter described in this specification can be implemented in a computing system that includes a back end component, for example, as a data server, or that includes a middleware component, for example, an application server. Moreover, the computing system can include a front-end component, for example, a client computer having one or both of a graphical user interface or a Web browser through which a user can interact with the computer. The components of the system can be interconnected by any form or medium of wireline or wireless digital data communication (or a combination of data communication) in a communication network. Examples of communication networks include a local area network (LAN), a radio access network (RAN), a metropolitan area network (MAN), a wide area network (WAN), Worldwide Interoperability for Microwave Access (WIMAX), a wireless local area network (WLAN) (for example, using 802.11 a/b/g/n or 802.20 or a combination of protocols), all or a portion of the Internet, or any other communication system or systems at one or more locations (or a combination of communication networks). The network can communicate with, for example, Internet Protocol (IP) packets, frame relay frames, asynchronous transfer mode (ATM) cells, voice, video, data, or a combination of communication types between network addresses.

The computing system can include clients and servers. A client and server can generally be remote from each other and can typically interact through a communication network. The relationship of client and server can arise by virtue of computer programs running on the respective computers and having a client-server relationship.

Cluster file systems can be any file system type accessible from multiple servers for read and update. Locking or consistency tracking may not be necessary since the locking of exchange file system can be done at application layer. Furthermore, Unicode data files can be different from non-Unicode data files.

While this specification contains many specific implementation details, these should not be construed as limitations on the scope of what may be claimed, but rather as descriptions of features that may be specific to particular implementations. Certain features that are described in this specification in the context of separate implementations can also be implemented, in combination, in a single implementation. Conversely, various features that are described in the context of a single implementation can also be implemented in multiple implementations, separately, or in any suitable sub-combination. Moreover, although previously described features may be described as acting in certain combinations and even initially claimed as such, one or more features from a claimed combination can, in some cases, be excised from the combination, and the claimed combination may be directed to a sub-combination or variation of a sub-combination.

Particular implementations of the subject matter have been described. Other implementations, alterations, and permutations of the described implementations are within the scope of the following claims as will be apparent to those skilled in the art. While operations are depicted in the drawings or claims in a particular order, this should not be understood as requiring that such operations be performed in the particular order shown or in sequential order, or that all illustrated operations be performed (some operations may be considered optional), to achieve desirable results. In certain circumstances, multitasking or parallel processing (or a combination of multitasking and parallel processing) may be advantageous and performed as deemed appropriate.

Moreover, the separation or integration of various system modules and components in the previously described implementations should not be understood as requiring such separation or integration in all implementations, and it should be understood that the described program components and systems can generally be integrated together in a single software product or packaged into multiple software products.

Accordingly, the previously described example implementations do not define or constrain the present disclosure. Other changes, substitutions, and alterations are also possible without departing from the spirit and scope of the present disclosure.

Furthermore, any claimed implementation is considered to be applicable to at least a computer-implemented method; a non-transitory, computer-readable medium storing computer-readable instructions to perform the computer-implemented method; and a computer system comprising a computer memory interoperably coupled with a hardware processor configured to perform the computer-implemented method or the instructions stored on the non-transitory, computer-readable medium.

A number of embodiments of these systems and methods have been described. Nevertheless, it will be understood that various modifications may be made without departing from the spirit and scope of this disclosure. Accordingly, other embodiments are within the scope of the following claims.

What is claimed is:

1. A method for evaluating a rock permeability by generating a 3D image model of a source rock in a subsurface formation, the method comprising:
   generating, using scanning electron microscopy, a binary 2D field of view image;
   selecting a plurality of regions from the generated binary 2D field of view image, wherein each region of the plurality of regions serves as an image seed;
   locating, by a processor of a computer, a plurality of pores from the plurality of image seeds;
   collecting pore data for each pore of the plurality of pores;
   characterizing the pore data for each pore of the plurality of pores;
   storing, in a memory of the computer, pore data for each pore from the plurality of pores;
   choosing an image seed of the plurality of image seeds as an initial slice of the 3D image model of the source rock;
   modulating the pore data for each pore of the plurality of pores relative to the plurality of pores from each image seed of the plurality of image seeds;
   generating, by the processor, a plurality of new images from the plurality of image seeds by reseeding, wherein the reseeding compensates for a loss of pores by reseeding pores according to a pore size distribution while approximately retaining the same number of pores as the initial slice; and
   combining, by the processor, the plurality of new images into a 3D volume to generate the 3D image model of the source rock.

2. The method of claim 1, wherein generating a binary 2D field of view image comprises identifying a plurality of pores as a first value and identifying the rest of the binary 2D field of view image as a second value.

3. The method of claim 1, wherein selecting a plurality of regions from the generated binary 2D field of view image comprises selecting regions with a pore size distribution similar to the pore size distribution from the generated binary 2D field of view image.

4. The method of claim 1, wherein collecting pore data for each pore of the plurality of pores comprises collecting a location, a size, shape, and a perimeter for each pore.

5. The method of claim 1, wherein the method further comprises size-dependent pore terminating process.

6. The method of claim 5, wherein the method further comprises retaining the data associated with the terminated pores that shrink below a specific size.

7. The method of claim 1, wherein the method further comprises selecting a plurality of random regions from the generated binary 2D field of view image.

8. The method of claim 1, wherein the method further comprises characterizing the pore data for each pore of the plurality of pores into small, medium, or large pores.

9. The method of claim 8, wherein reseeding the pores comprises when the pore count drops below a threshold, adding new small, medium, and large pores according to the pore size distribution.

10. The method of claim 1, wherein the method further comprises simulating permeability of the source rock.

11. The method of claim 1, wherein the method further comprises simulating electrical and thermal conductivity of the source rock.

12. The method of claim 1, wherein the method further comprises correlating the pore data to mechanical and mineralogical data of the source rock.

13. A computer program product residing on a non-transitory computer readable medium of a computer, the computer program product comprising instructions to:
generate, using scanning electron microscopy, a binary 2D field of view image;
select a plurality of regions from the generated binary 2D field of view image, wherein each region of the plurality of regions serves as an image seed;
locate, by a processor of the computer, a plurality of pores from each image seed of a plurality of image seeds;
collect pore data for each pore of the plurality of pores;
characterize the pore data for each pore of the plurality of pores;
store, in a memory of the computer, pore data for each pore from the plurality of pores;
choose an image seed of the plurality of image seeds as an initial slice of the 3D image model of the source rock;
modulate the pore data for each pore of the plurality of pores relative to the plurality of pores from each image seed of the plurality of image seeds;
generate, by the processor, a plurality of new images from the plurality of image seeds by reseeding, wherein the reseeding compensates for a loss of pores by reseeding pores according to a pore size distribution while approximately retaining the same number of pores as the initial slice; and
combine, by the processor, the plurality of new images into a 3D volume to generate the 3D image model of the source rock.

14. The computer program product of claim 13, wherein generating a binary 2D field of view image comprises identifying a plurality of pores as 1 or white color and identifying the rest of the binary 2D field of view image as 0 or black color.

15. The computer program product of claim 13, wherein the pore size distribution is determined from the generated binary 2D field of view image, and selecting a plurality of regions from the generated binary 2D field of view image comprises selecting regions with a pore size distribution similar to the pore size distribution from the generated binary 2D field of view image.

16. The computer program product of claim 13, wherein collecting pore data for each pore of the plurality of pores comprises collecting a location, a size, shape, and a perimeter for each pore.

17. The computer program product of claim 13, wherein the method further comprises size-dependent pore terminating process.

18. The computer program product of claim 13, wherein the method further comprises selecting a plurality of random regions from the generated binary 2D field of view image.

19. The computer program product of claim 13, wherein the method further comprises characterizing the pore data for each pore of the plurality of pores into small, medium, or large pores.

20. The computer program product of claim 13, wherein reseeding the pores comprises when the pore count drops below a threshold, adding new small, medium, and large pores according to the pore size distribution.

* * * * *